United States Patent [19]
Veronese et al.

[11] Patent Number: 5,629,384
[45] Date of Patent: May 13, 1997

[54] POLYMERS OF N-ACRYLOYLMORPHOLINE ACTIVATED AT ONE END AND CONJUGATES WITH BIOACTIVE MATERIALS AND SURFACES

[75] Inventors: Francesco M. Veronese; Oddone Schiavon; Paolo Caliceti, all of Padua; Luciana Sartore, Marano Vic.; Elisabetta Ranucci, Brescia; Paolo Ferruti, Milan, all of Italy

[73] Assignee: Consiglio Nazionale delle Ricerche, Italy

[21] Appl. No.: 243,869

[22] Filed: May 17, 1994

[51] Int. Cl.⁶ .............................. C08F 8/00; C08F 20/58; C08F 20/60
[52] U.S. Cl. .......................... 525/326.8; 526/89; 526/234
[58] Field of Search ................... 526/89, 234; 525/326.8

[56] References Cited

U.S. PATENT DOCUMENTS

| | | |
|---|---|---|
| 4,179,337 | 12/1979 | Davis et al. . |
| 4,296,097 | 10/1981 | Lee et al. . |
| 4,430,260 | 2/1984 | Lee et al. . |
| 4,670,417 | 6/1987 | Iwasaki et al. . |
| 4,766,106 | 8/1988 | Katre et al. . |
| 4,791,192 | 12/1988 | Nakagawa et al. . |
| 4,902,502 | 2/1990 | Nitecki et al. . |
| 4,917,888 | 4/1990 | Katre et al. . |
| 4,931,544 | 6/1990 | Katre et al. . |
| 5,080,891 | 1/1992 | Saifer et al. . |
| 5,089,261 | 2/1992 | Nitecki et al. . |
| 5,122,614 | 6/1992 | Zalipsky . |
| 5,153,265 | 10/1992 | Shadle et al. . |
| 5,162,430 | 11/1992 | Rhee et al. . |
| 5,344,880 | 9/1994 | Nambu et al. ............... 528/16 |
| 5,420,004 | 5/1995 | Fujita et al. ............... 430/559 |

FOREIGN PATENT DOCUMENTS

| | | |
|---|---|---|
| 0247860 | of 0000 | European Pat. Off. . |
| WO87/00056 | 1/1987 | WIPO . |
| WO90/04606 | 5/1990 | WIPO . |
| WO90/04384 | 5/1990 | WIPO . |
| WO90/04650 | 5/1990 | WIPO . |
| WO90/15628 | 12/1990 | WIPO . |
| WO91/07190 | 5/1991 | WIPO . |
| WO92/04384 | 3/1992 | WIPO . |
| WO92/13095 | 8/1992 | WIPO . |
| WO92/16555 | 10/1992 | WIPO . |

OTHER PUBLICATIONS

A. Abuchoswki et al., "Soluble Polymer–Enzyme Adducts", *Enzymes as Drugs*, J.S. Holcenbery and J. Roberts ed., Wiley & sons pp. 367–383 (Apr., 1981).

P. Ferruti et al., "Oligomeric Prodrugs", *High Performance Biomaterials: A Comprehensive Guide to Medical & Pharmaceutical Applications*, M. Szycher Ed., Technomics Pub. Inc., pp. 539–572 (Aug., 1991).

P. Caliceti et al., "Preparation and Properties of Monomethoxypoly (ethylene glycol)–Doxorubicine Conjugates Linked by an Amino Acid or Peptide as Spacer," *IL Farmaco*, 48,919–932 (Jul., 1993).

E.W. Merrill, "Poly(ethylene oxide) and Blood Contact: A Chronicle of One Laboratory," *Poly(Ethylene Glycol) Chemistry: Biotechnical and Biomedical Applications*, J.M. Harris ed., pp. 199–220 (Jul., 1992).

C.-G. Gölander et al., "Properties of Immobilized PEG Films and the Interaction with Proteins: Experiments and Modeling," *Poly(Ethylene Glycol) Chemistry: Biotechnical and Biomedical Applications*, pp. 221–245 (Jul., 1992).

D.E. Brooks et al., "PEG–Derivatized Ligands with Hydrophobic and Immunological Specificity: Applications in Cell Separation," *Poly(Ethylene Glycol) Chemistry: Biotechnical and Biomedical Applications*, pp.57–71 (Jul., 1992).

G. Johansson, "Affinity Partitioning in PEG–Containing Two–Phase Systems," *Poly(Ethylene Glycol) Chemistry: Biotechnical and Biomedical Applications*, pp. 73–84 (Jul., 1992).

D. Papahadjopoulos et al., "Sterically Stabilized Liposomes: Improvements in Pharmacokinetics and Antitumor Therapeutic Efficacy," *Proc. Natl. Acad. Sci. USA*, vol. 88, pp. 11460–11464 (Dec., 1991).

G.M. Bonora, "Large Scale, Liquid Phase Synthesis of Oligonucleotides by the Phosphoramidite Approach," *Nucleic Acids Research*, vol. 21, No. 5, pp. 1213–1217 (Mar., 1993).

L. Illum et al., "The Effect of Hydrophilic Coatings on the Uptake of Colloidal Particles by the Liver and by Peritoneal Macrophages," *International Journal of Pharmaceutics*, 29, pp. 53–65 (Mar., 1986).

Y. Inada et al., "Application of Polyethylene Glycol–Modified Enzymes in Biotechnological Processes: Organic Solvent–Soluble Enzymes," *Elsevier Science Publishers B.V.*, pp. 190–194 (Jul., 1986).

(List continued on next page.)

*Primary Examiner*—Jeffrey C. Mullis
*Attorney, Agent, or Firm*—Bell, Seltzer, Park & Gibson, P.A.

[57] ABSTRACT

Polymers of the monomer N-acryloylmorpholine having a single reactive moiety at one end of the polymer chain have the following structure:

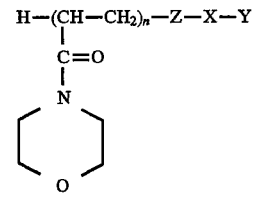

wherein -Z-X-Y is a polymer capping moiety, such as mercaptan, X represents a saturated residue of a linear or branched aliphatic series of the general structure —$C_rH_{2r}$— in which r is an integer from 1 to about 12, Y is a reactive moiety and typically will be one of the reactive moieties commonly known in PEG chemistry, such as an —OH, —COOH, or —$NH_2$ group, Z is a moiety that readily reacts to cap a polymer free radical, and n is an integer from about 6 to 280, which yields a number average molecular weight ("$M_n$") of from about 1,000 to 40,000. The monofunctional polymer is a suitable alternative to monofunctional PEG for modification of substances having biological and biotechnical applications.

19 Claims, No Drawings

OTHER PUBLICATIONS

F.M. Veronese et al., "Surface Modification of Proteins by Covalent Binding of Acrylic Polymers," *Appl. Biochem. Biotechnol.*, vol. 11, pp. 269–277 (Aug., 1985).

F. Paolietti et al., "A Sensitive Spectrophotometric Method for the Determination of Superoxide Dismutase Activity in Tissue Extracts," *Analytical Biochemistry*, 154, pp. 536–541 (May, 1986).

A.G. Gornall et al., "Determination of Serum Proteins by Means of the Biuret Reaction," *J. Biol. Chem.*, 177, pp. 751–766 (Feb., 1949).

A.F.S.A. Habeeb, "Determination of Free Amino Groups in Proteins by Trinitrobenzenesulfonic Acid," *Analytical Biochemistry* 14, pp. 328–336 (Mar., 1966).

J.J. Hagan et al., "Measurement of Arginase Activity," *Analytical Biochemistry*, 22, pp. 518–524 (Mar., 1968).

H.N. Jayaram et al., "A Simple and Rapid Method for the Estimation of L-Asparaginase in Chromatographic and Electrophoretic Effluents: Comparison with Other Methods," *Analytical Biochemistry*, 59, pp. 327–346 (Jun., 1974).

R.F. Beers, Jr. et al., "A Spectrophotometric Method for Measuring the Breakdown of Hydrogen Peroxide by Catalase," *J. Biol. Chem.*, 195, pp. 133–140 (Mar., 1952).

E.M. Crook et al., "Spectrophotometric Assay of Bovine Pancreatic Ribonuclease by the use of Cytidine 2':3'-Phosphate," *Biochem. J.*, 74, pp. 234–238 (Feb., 1960).

S.H. Pomerantz, "Separation, Purification, and Properties of Two Tyrosinases from Hamster Melanoma," *J. Biol. Chem.*, vol. 238, pp. 2351–2357 (Jul., 1963).

M. Laskowski, "Trypsinogen and Trypsin," *Methods Enzymol.*, 2, pp. 26–36 (1955).

J.L. Mahler, "A New Bacterial Uricase for Uric Acid Determination," *Analytical Biochemistry*, 38, pp. 65–84 (Nov., 1970).

POLYMERS OF N-ACRYLOYLMORPHOLINE ACTIVATED AT ONE END AND CONJUGATES WITH BIOACTIVE MATERIALS AND SURFACES

FIELD OF THE INVENTION

This invention relates to polymers having a reactive moiety at at least one terminus thereof, their synthesis, activation of the reactive moiety for conjugation with bioactive materials and surfaces, and conjugates thereof with bioactive materials and surfaces. More particularly, this invention relates to amphiphilic polymers activated at one end and their conjugates with bioactive materials and surfaces for biological and biotechnical applications.

BACKGROUND OF THE INVENTION

Polymers are of great interest that are soluble both in organic solvents and in water (i.e., amphiphilic polymers) and that are suitably activated at the termini to obtain ready linkage to compounds with biological activity. Amphiphilic polymer derivatives have been proposed for modification of the physical, chemical, and pharmacological properties of biologically active materials and surfaces for biomaterials.

For example, surface modification of enzymes and polypeptides as potential therapeutic drugs is proposed by A. Abuchoswki and F. F. Davis, in "Enzymes as Drugs" J. S. Holcenbery and J. Roberts ed , Wiley & Sons, p. 367—384 (1981). It is known that polymer derivatized proteins increase circulation life in the body, decrease immunogenic reaction, and allow some targeting.

Amphiphilic polymers have been proposed for the preparation of prodrugs as illustrated by P. Ferruti and E. Ranucci in "High Performance Biomaterials", M. Szycher Ed., Technomics Pub Inc., p. 539–572 (1991); and by P. Caliceti, C. Monfardini, L. Sartore, O. Schiavon, F. Baccichetti, F. Carlassare and F.M. Veronese, in "Preparation and Properties of Monomethoxypoly (ethylene glycol)-Doxorubicine Conjugates Linked by an Amino Acid or Peptide as Spacer", 11 Farmaco, 48, 919–9,32 (1993).

Biocompatible polymers have been proposed for modifying surfaces as shown in E. W. Merrill, in "Poly(ethylene oxide) and Blood Contact: A Chronicle of One Laboratory; in Poly(ethylene glycol) Chemistry: Biotechnical and Biomedical Applications," J. M. Harris ed., p. 199–220 (1992), Plenum Publishing Corporation, New York; C. G. Golander; and by J. N. Herron, K. Lim, P. Stenius and J. D. Andrade in "Properties of Immobilized PEG Film and Interaction with Protein: Experiments and Modelling," p. 221–245 (1992) ibidem.

Bioseparation by two phase partioning has been proposed with amphiphilic polymers as shown by D. E. Brooks, J. M. Van Alstine, K. A. Sharp and S. J. Stocks, in "PEG-Derivatized Ligands with Hydrophobic and Immunological Specificity: Applications in Cell Separation," p. 57–71 (1992) ibidem; and by G. Johansson in "Affinity Partioning in PEG-Containing Two-Phase System," p. 73–84 (1992) ibidem.

Liposomes have been proposed for modification with amphiphilic polymers as shown by D. Papahadjopoulos, T. M. Allen, A. Gabizon, E. Mayhew, K. Matthay, S. K. Huang, K. D. Lee, M.C. Woodle, D. D. Lasic, C. Redemann and F. J. Martin in "Sterically Stablished Liposomes: Improvements in Pharmacokinetics and Antitumor Therapeutic Efficacy," Pro. Natl. Acad. Sci. 88, 11460–11464 (1991).

Amphiphilic polymers have been proposed for liquid phase synthesis of oligomeric peptides and nucleotides as shown by G. M. Bonora, G. Biancotto, M. Maffini, C. L. Scremin in "Large Scale, Liquid Phase Synthesis of Oligonucleotides by the Phosphoramidite Approach," Nucleic Acids Research, 21, 1213–1217 (1993).

Colloidal particles have been proposed for coating with a hydrophilic coating of an amphiphilic polymer for controlled delivery as illustrated in L. Illum, I. M. Hunneyball, and. S. S. Davis, Inter. J. Pharm., 29, 53–65 (1986).

Enzymes have been proposed for modification with amphiphilic polymers for biocatalysis in organic solvents as shown by Y. Inada, K. Takahashi, T. Yoshimoto, A. Ajima, A. Matsushima and Y. Saito in "Application of Poly (ethyleneglycol)-Modified Enzymes in Biotechnological Processes: Organic Solvent-Soluble Enzymes", Tibtech 4 190–194 (1986)

Several polymers have been studied in connection with the above uses of amphiphilic polymers. Among these polymers are the following: dextran, polyalanine, polyacrylic and polymaleic polymers, poly(ethylene glycol) of various molecular weights, and others. Poly(ethylene glycol) ("PEG") has received the most interest because of its absence of toxicity, antigenicity, immunogenicity, for its degree of amphiphilicity. PEG can be activated at each terminus to be bifunctional. PEG can also be modified to have a reactive moiety at one end. This reactive moiety can be activated for attachment of the monofunctional PEG to biomaterials. Monofunctional PEG avoids, at least in the case of polypeptides, multiple binding with cross linking and aggregation.

Amphilic polymers different from PEG have been functionalized and conjugated with protein. For example, copolymers of acrylic acid with N-acryloylmorpholine ("AcM") have been prepared and the reactive sites activated by conversion to the N-hydroxysuccinimide active ester. These copolymers have multiple active sites and are polyfunctional. The polyfunctional copolymers have been attached to proteins as illustrated by F. M. Veronese, R. Largajolli, C. Visco, P. Ferruti and A. Minucci, J. in Appl. Biochem. Biotechnol. 11, 269–277 (1985). The copolymer modified proteins are soluble in water and many organic solvents and have been shown to be nontoxic by P. Ferruti and E. Ranucci in "High Performance Biomaterials" in M. Szycher ed., Technomics, p. 539–572 (1991). However, the copolymers have the disadvantage of being activated along the chain, which can lead to problems such as aggregation, cross linking and complex mixtures.

SUMMARY OF THE INVENTION

The present invention includes the synthesis and fractionation of polymers of the monomer N-acryloylmorpholine having a single reactive moiety at one end of the polymer chain. The single reactive moiety of polymeric N-acryloylmorpholine ("PAcM") can be activated for selective monofunctional attachment of PAcM to various surfaces and molecules, including biomaterials and bioactive substances such as enzymes, polypeptides, drugs, nucleosides, and phospholipids.

The invention includes the polymer having the single reactive group, its synthesis, its activation to a monofunctional polymer for conjugation with surfaces and molecules, and the conjugates of surfaces and molecules formed with the polymer. Proteins and enzymes modified with monofunctional PAcM are amphiphilic and substantially reduced in immunogenicity.

Polymeric N-acryloylmorpholine has the following structure:

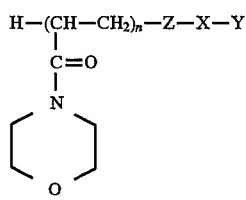

In the structure shown for PAcM, X represents a saturated residue of a linear or branched aliphatic series of the general structure —$C_rH_{2r}$— in which r is an integer from 1 to about 12, Y is a reactive moiety and typically will be one of the reactive moieties commonly known in PEG chemistry, such as an —OH, —COOH, or —NH$_2$ group, but can be any of a broad array of reactive moieties, Z is a moiety that readily reacts to cap a polymer free radical, and n is an integer from about 6 to 280, which yields a number average molecular weight ("$M_n$") of from about 1,000 to 40,000.

Thus, among other things, the invention provides a monofunctional polymer that is a suitable alternative to monofunctional PEG for modification of substances having biological and biotechnical applications.

DETAILED DESCRIPTION OF THE PREFERRED EMBODIMENTS

The synthesis of monofunctional PAcM proceeds by polymerization of monomeric N-acryloylmorpholine using any of a variety of initiators known in polymer chemistry to the skilled artisan to polymerize the carbon/carbon double bond. Polymerization typically is initiated with free radical initiators such as N,N'azobisisobutyronitrile ("AIBN") as follows:

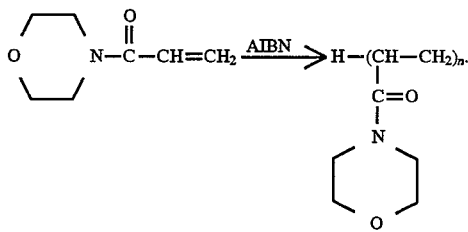

The synthesis proceeds by polymerization of monomeric N-acryloylmorpholine in the presence of a capping agent, such as mercaptan, which can also be referred to as a chain transfer agent. The capping agent provides a reactive moiety for the PAcM and controls molecular weight by controlling the polymer chain length. The reaction is as follows:

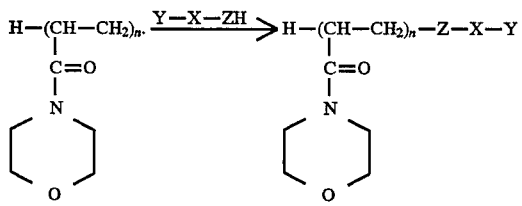

The reactive moiety at the end of the polymer chain, Y, can be selected by choice of the appropriate capping agent. Any of the variety of capping or chain transfer agents known in connection with polymer chemistry should be suitable for terminating polymerization, controlling molecular weight, and providing a reactive moiety for the capped polymer end group. For example, chlorine compounds and mercaptans can be used. Also, any of the reactive moieties typically known in PEG chemistry should be useful in connection with the capping agent for providing the reactive moiety at the terminus of the capped polymer. The capping agents can be generally represented structurally as Y—X—ZH, where Y is a reactive moiety, X is a saturated residue of a linear or branched aliphatic series of the general structure —$C_rH_{2r}$—, in which r is an integer from 1 to about 12, and Z is a moiety that readily reacts to cap a polymer free radical.

Specific examples shown below utilize 2-mercaptoethanol, 2-mercaptoacetic acid, and 2-mercaptoethylamine to introduce alcohol, carboxyl, and amino end groups, respectively. Capping of the polymer with mercaptan can be represented generally as:

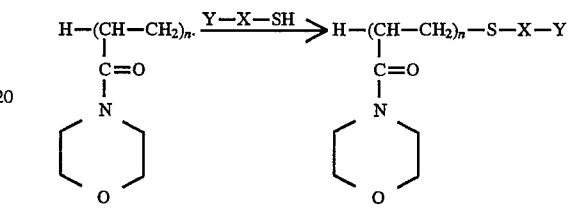

In all cases, polymerizations were performed under slightly acidic conditions to avoid hydrogen addition to the AcM double bond.

The molecular weight of the polymer is controlled by controlling the amount of capping agent in which the polymerization takes place. The molecular weight of the polymer is reduced as the relative concentration of the chain-transfer agent is increased.

The molecular weight of the resulting oligomers (PAcM-OH, PAcMCOOH and PAcM-NH2) does not vary appreciably with polymerization yield. To give an example, AcM was polymerized at 60° C. in aqueous solution (20%) with AIBN as initiator. During polymerization, aliquots were taken, the polymerization yield was determined, and a GPC tracing obtained. No variation in polymer molecular weight was indicated.

After the polymer is synthesized, the reactive terminal groups can be modified by further reaction ("functionalized" or "activated") to give reactive moieties active for attaching the polymers to molecules and surfaces of interest.

The following examples illustrate the invention.

EXAMPLE 1

Synthesis of PAcM-S-CH$_2$CH$_2$-OH

A. A mixture of N-acryloylmorpholine monomer (28.2 g, 0.2M) and N,N'azobisisobutyronitrile (0.56 g) was dissolved in a mixture of 0.1M aqueous acetic acid (50 ml) and 2-mercaptoethanol (0.38g, 0.005M). This gives a ratio of monomer to chain transfer agent of 40 to 1. After careful flushing with nitrogen, the mixture was maintained under a nitrogen atmosphere for 24 hours at 60° C. The reaction mixture was then lyophilized, extracted with dichloromethane, and filtered. The organic phase was then diluted with excess ether. The product precipitated out as a white powder. Yield was almost quantitative. Intrinsic viscosity [η]=0.09 dl/g. The polymer is represented in the following discussion as PAcM-OH.

B. The same procedure as in Example 1A was followed with the only difference being that a monomer to chain transfer agent ratio of 5 to 1 was used. Intrinsic viscosity was

[η]=0,025 dl/g. Note that the lower viscosity obtained in this example, relative to example 1A, indicates that the expected lower molecular weight is obtained.

EXAMPLE 2

Synthesis of PAcM-S-CH$_2$-COOH

A. The same procedure as in Example 1A was followed except that 2-mercaptoacetic acid is used as chain-transfer agent. Also water is used as solvent instead of acetic acid. Yield was almost quantitative. Intrinsic viscosity was [η]= 0.08 dl/g. This polymer is represented as PAcM-COOH.

B. The same procedure as in Example 2A was followed with the only difference being that a monomer to chain transfer agent ratio of 5 to 1 was used. An intrinsic viscosity [η] of 0.024 dl/g was found, consistent with a reduction in molecular weight relative to Example 2A.

EXAMPLE 3

Synthesis of PAcM-S-CH$_2$CH$_{2-NH2}$

The same procedure as in Example 1A was followed except that 2-aminoethylamine (cysteamine) was used as chain-transfer agent. Yield was almost quantitative. Intrinsic viscosity [η]=0.08 dl/g. This polymer is represented as PAcM-NH$_2$.

EXAMPLE 4

Synthesis of PAcM-S-CH$_2$CH$_2$-COOH

The same procedure as in Example 2A was followed except that 2-mercaptoacetic acid was substituted with an equimolecular quantity of 3-mercaptopropionic acid. Yield was almost quantitative. Intrinsic viscosity [η]=0.08 dl/g. This polymer is represented as PAcM-COOH.

EXAMPLE 5

Fractionation of PAcM-COOH by Gel Permeation Chromatography

The fractionation of PAcM-COOH was carried out by size exclusion chromatography on a Pharmacia Bio Gel P 60 column (5×50 cm), with water as mobile phase at a flow rate of 20 ml/h. The PAcM-COOH sample from example 2 (1 g) was dissolved in water (5 ml) and injected into the column after 30 min stirring. The fractions were examined by UV-VIS spectrometry at 220 nm and iodine test according to Sims and Snape, Anal. Biochem. 107, p. 60–63 (1980). The PAcM elution profile was a symmetrical peak. Three main fractions were collected, corresponding to the elution volume of 220–400 ml, 410–510 ml and 520–640 ml. The three fractions, A, B, and C respectively, were lyophilized and reprecipitated from CH$_2$Cl$_2$/Et$_2$O. The fractions were characterized by potentiometric titration and elemental analysis in Table 1.

TABLE 1

Number average molecular weight of PAcM-COOH fractions obtained through gel filtration chromatography. Molecule weight was determined through end-group titration.

| Fractions | M$_n$(D) |
|---|---|
| (A) | 7100 |
| (B) | 5000 |
| (C) | 2100 |
| Raw material | 4100 |

The same procedure was followed for PAcM-OH fractionation and similar results were obtained.

EXAMPLE 6

Fractionation of PAcM-COOH by Solvent-Cosolvent Precipitation

PAcM-COOH (example 1A) (5 g) was dissolved in 110 ml of a mixture of isopropyl alcohol and CH$_2$CL$_2$(ratio 8/3). Fractions of the polymer were precipitated through successive additions of dry diethylether (30, 35, 95 ml). The polymer that precipitated after each addition was separated through centrifugation at 5,000 rpm, while the last fraction was obtained by evaporating the solvent under vacuum. The fractions were dissolved in CH$_2$Cl$_2$ and reprecipitated with dry ethyl ether. The products were characterized through titration of the carboxyl group with 0.01N NaOH and the results are reported in Table 2.

TABLE 2

Number average molecular weight (M$_n$) of PAcM-COOH fractions obtained through fractional precipitation. Molecular weight was determined through end group titration with 0.01N NaOH.

| Fractions | M$_n$(D) |
|---|---|
| 1 | 7000 |
| 2 | 6000 |
| 3 | 4500 |
| 4 | 2400 |

Polymer fractions were also characterized by gel filtration with a Biogel Sec 30 XL column (BioRad) operated on an HPLC system and eluted with Na$_2$SO$_4$ 0.1M, NaH$_2$PO$_4$ 0.1M, pH 6.8 buffer.

Following the same method of fractional precipitation the PAcM-OH polymer was purified to obtain fractions with similar properties.

In the following examples on molecule and surface modification, the polymer fraction used is the one with average molecular weight of approximately 6,000 D, which is the second fraction obtained by precipitation (Table 2) and the fraction B obtained by gel filtration (Table 1).

EXAMPLE 7

Activation of PAcM-OH with p-nitrophenylchloroformate 1.0 g. (0.2 mmoles) PAcM-OH (approximately 5000 MW, obtained through gel filtration), was dissolved in the minimum amount of dry CHCl$_3$, dried with CaH$_2$, and subsequently 81 mg (0.4 mmoles) p-nitrophenylchloroformate were added while pH 8.0 was maintained with triethylamine (this was done by placing a drop of the organic reaction mixture on wet pH paper). The mixture was kept overnight in the dark at room temperature under stirring and then added to ethyl ether solution under stirring. The resulting precipitate was filtered, dried with $P_2O_5$ and recrystallized from $CH_2Cl_2/Et_2O$. 1.2 g. of product was obtained with 97% yield.

EXAMPLE 8

Activation of PAcM-COOH to obtain PAcM-COOSu 0.9 g. (0.15 mmoles) PAcM-COOH (6000 D) was dissolved in the minimum amount of dry $CH_2Cl_2$ and cooled in ice bath. 35 mg (0.3 mmoles) of N-hydroxysuccinimide and 62 mg (0.3 mmoles) dicyclohexylcarbodiimide were added; the reaction temperature was permitted to rise to room temperature and the solution stirred for 4 hours. Dicyclohexyl urea was removed by filtration and the product poly (acryloylmorpholine) succinimidyl ester (PAcM-COOSu) was isolated by precipitation in diethylether. 0.9 g (98% yield) were obtained after a second precipitation from $CH_2Cl_2$/ether.

It should be recognized that a wide variety of active moieties functional for attachment to bioactive compounds and surfaces is available in PEG chemistry and that the reactive moieties on PAcM should also be activatable through similar techniques. For active moieties for biological and biotechnical applications, the substituents would typically be selected from reactive moieties typically used in PEG chemistry to activate PEG such as sulfone (such as vinyl sulfone or chloroethylsulfone) the aldehydes, trifluoroethylsulfonate, which is also sometimes called tresylate, n-hydroxylsuccinimide ester, cyanuric chloride, cyanuric fluoride, acyl azide, succinate, the p-diazo benzyl group, the 3-(p-diazophenyloxy)-2-hydroxy propyloxy group, and others.

Examples of active moieties are shown in David et al. U.S. Pat. No. 4,179,337; Lee et al. U.S. Pat. Nos. 4,296,097 and 4,430,260; Iwasaki et al. U.S. Pat. No. 4,670,417; Katre et al. U.S. Pat. Nos. 4,766,106; 4,917,888; and 4,931,544; Nakagawa et al. U.S. Pat. No. 4,791,192; Nitecki et al. U.S. Pat. Nos. 4,902,502 and 5,089,261; Saifer U.S. Pat. No. 5,080,891; Zalipsky U.S. Pat. No. 5,122,614; Shadle et al. U.S. Pat. No. 5,153,265; Rhee et al. U.S. Pat. No. 5,162,430; European Pat. Application Publication No. 0 247 860; and PCT International Application Nos. US86/01252; GB89/01261; GB89/01262; GB89/01263; US90/03252; US90/06843; US91/06103; US92/00432; and US92/02047; the contents of which are incorporated herein by reference.

EXAMPLE 9

Modification of superoxide dismutase with PAcM-COOSu 5 mg of superoxide dismutase (SOD) from bovine liver were dissolved in 2 ml 0.2M borate buffer, pH 8.0, and PAcM-COOSu (see example 8) (50 mg) (molar ratio of protein amino groups to polymer of 1/3) was added under stirring. The mixture was kept under stirring at room temperature for 1 hour, and then the polymer-enzyme adduct was purified by ultrafiltration in an Amicon system with a PM 10 membrane. The polymer-enzyme adduct was further purified through gel filtration chromatography with a Superose 12 analytical column (Pharmacia), eluted with 0.01M $Na_2HPO_4/NaH_2PO_4$, 0.15M NaCl, pH 7.2 buffer operating on an FPLC instrument (Pharmacia). The eluted fractions were analyzed by UV-VIS spectrometry at 258 nm to verify protein content.

The SOD enzymatic activity assay of Paoletti was used as shown in F. Paoletti, A. Aldinucci, A. Mocali, A. Caparrini, Anal Biochem., 154, 536–541 (1986). Iodine assay was used to determine polymer content.

Fractions corresponding to elution of the conjugate (i.e, the fractions showing absorbance at 258 nm, iodine reactivity and enzymatic activity) were collected and concentrated. Protein concentration of the purified product (namely SOD-PAcM) was evaluated by biuret assay according to A. G. Gornall, C. J. Baldwell and David, J. Biol. Chem., 177, 651 (1949). Residual activity was measured through enzymatic assay. The number of polymer chains bound to each enzyme molecule was determined through Habeeb assay according to A.F.S.A Habeeb, Anal. Biochem., 14, 328–336 (1966). Fifty-two percent of the available protein amino groups were modified by polymer attachment, and the residual enzymatic activity was 55%.

In the following examples amounts of PAcM-enzyme conjugates are expressed in terms of enzyme content.

EXAMPLE: 10

Modification Of other enzymes with PAcM-COOSu

To demonstrate generality of enzyme modification with PAcM, a set of therapeutically important enzymes (asparaginase, tyrosinase, uricase, arginase, catalase, trypsine, ribonuclease A and lipase) were modified with PAcM-COOSu. In each case 10 mg of enzyme was used and the amount of PAcM-COOSu was varied to maintain a molar ratio of polymer to protein amino groups of 3/1. The following methods were used to evaluate the residual enzymatic activity:

arginase: Hagan J. J. et al., Anal. Chem., 22, 518 (1968);
asparaginase: Jayaran H. N et al., Anal. Biochem. 59, 327–346 (1974); catalase: Beers R. F. et al., J. Biol. Chem., 195, 133 (1952);
ribonuclease: Crook E. M. et al., Biochem. J. 74, 234 (1960);
tyrosinase: Pomerantz S. H. et al., J. Biol. Chem., 238, 2351–2357 (1963);
trypsin: Leskowski M., Methods Enzymol., 2, 26–36 (1955);
uricase: Mahler J. L., Anal. Biochem., 38, 65–84 (1970).

The amount of protein in the conjugates was evaluated by the biuret method. All the proteins studied were extensively modified by polymer attachment. Except for the case of ribonuclease, enzymatic activity was not significantly reduced by polymer attachment. As an example, tyrosinase with 70% of its lysines modified, maintained 100% of the starting activity. In the exceptional case of ribonuclease, the adduct with 78% of lysines modified with polymer gave a residual activity of only 31%.

EXAMPLE 11

Pharmacokinetic studies of SOD-PAcM and RNase-PAcM

To monitor the pharmacokinetics (i.e, the body distribution and elimination) to PAcM-enzyme conjugates, two PAcM-enzymes (superoxidedismutase or SOD, and ribonuclease, or RNase) were labelled with radioactive tritium and injected into mice for sampling.

A. Preparation of labelled native and polymer-modified enzymes 10 mg of native (i.e., unmodified) enzyme (SOD or RNase) or polymerenzyme conjugate (SOD-PAcM or RNase-PAcM) were dissolved in 2 ml of sodium borate buffer (0.2M, pH 8.0). N-succinimidyl[2,3-$^3$H] propionate (1.3×10⁸ DMP/mg) was added to this solution at a concentration of 0.5, moles of propionate per mole of free amino group. After 30 minutes stirring at room temperature, the solution was purified by ultrafiltration in an Amicon system with a PM 10 membrane. The labelled material was finally purified by gel chromatography on a Superose 12 column under the same conditions as described in Example 9. Protein concentration, polymer content, enzymatic activity and radioactivity (scintillation counting was used) were evaluated on the fractions eluted. The SOD-PAcM conjugate had a radioactivity of $5.32 \times 10^5$ DPM/mg and the RNase-PAcM conjugate had a radioactivity of $5.5.3 \times 10^5$ DPM/mg; these results demonstrate attachment of the tritium labelled propionate to the enzymes. For the native enzymes the radioactivity of SOD was $1.13 \times 10^6$ DPM/mg and that of RNase was $9.11 \times 10^4$ DMP/mg B. Animal experiments The tritium labelled proteins were administered in the following manner. 1 mg of native enzyme (RNase or SOD) or polymer-enzyme conjugate (SOD-PAcM or RNase-PAcM) was dissolved in 200 μl of pH 7.2 buffer (0.1M Na₂HPO₄/NaH₂PO₄, 0.15M NaCl) and injected into the caudal vein of male rats (Wistar line, weighing 200 to 220 g, fed "ad libitum"). Blood was taken at fixed times from the heart with a heparinized syringe, under ether anaesthesia. The blood was then centrifuged at 3,500 rpm for 3 minutes, and the radioactivity level of 100 μl of plasma was measured. These studies were conducted in duplicate. The values obtained, expressed as a percentage of the value obtained at one minute after inoculation, are reported in Table 3. Pharmacokinetic profiles for native enzymes and enzyme-polymer conjugates are given in FIGS. 1 and 2.

The $T_{1/2}$ and $T_{10\%}$ values given in Table 3 represent the time required for the radioactivity level in the blood to drop to 50% and 10% of the value at one minute, respectively. The $T_{1/2}\alpha$, and $T_{1/2}\beta$ values represent kinetic constants of the so-called distribution phase (the time for distribution in the body) and the so-called elimination phase (the time for elimination from the body). As shown in Table 3, the PAcM-modified enzymes show larger values for the various parameters, demonstrating that the enzyme-polymer conjugates are cleared much more slowly from the blood than the native enzymes.

TABLE 3

Pharmacokinetic parameters for RNase, SOD, and PAcM-modified enzymes after administration to rats.

| Molecular species | $T_{1/2}$ | $T_{10\%}$ | $T_{1/2\alpha}$ | $T_{1/2\beta}$ |
|---|---|---|---|---|
| [³H] RNase | 8 min | 50 min | — | — |
| [³H] RNase-PAcM | 4.7 h | 75 h | 10 min | 26 h |
| [³H] SOD | 5 min | 66 min | — | — |
| [³H] SOD PAcM | 6.0 h | 120 min | 30 min | 46 h |

EXAMPLE 12

Antigenicity of enzyme-polymer conjugate evaluated by immunoprecipitation studies Native RNase, native SOD, PAcM-RNase, or PAcM-SOD was dissolved in pH 7.4 buffer (Tris HCl 0.01M, NaCl 10.15M) to a concentration of 0.2 mg/ml. Variable amounts (0 to 60 μl) of this solution was added to 90 μl of freshly prepared rabbit antiserum immunized against native enzyme. The final volume was brought to 150 μl with the same buffer. Samples were incubated for 30 minutes at room temperature, and then 20 hours at 4° C. The samples were then centrifuged for 15 minutes at 5,000 rpm, and the precipitate was washed times with 800 μl of buffer. The precipitate was finally dissolved with 300 μl of 0.1M NaOH and the radioactivity evaluated., in duplicate, for 100 μl of solution.

The results of these measurements are given in FIGS. 4 and 5. These Figures demonstrate a sharply decreased antigenic response for PAcM-SOD and PAcM-RNase as compared to the native enzymes.

EXAMPLE 13

PAcM drug conjugates

The following experiments show that PAcM can be attached to a variety of drugs of great pharmaceutical importance.

A. PAcM-Doxorubicine

Doxorubicine (120 mg, 0.2 mM) was dissolved in dimethylsulfoxide (3 ml) and added to 10 ml of methylene chloride solution of PAcM-COOSu (described above in Example 8, 600 mg, 0.1 mM), while the pH was adjusted to 8 with triethylamine. This pH measurement was made by placing a drop of the methylene-chloride solution onto a piece of damp pH paper. After overnight stirring at room temperature in the dark, the product was isolated by precipitation by addition of the solution to an excess of diethyl ether. One mmole of the precipitate was slowly dissolved in 2 ml aqueous solution, pH 8. The mixture was stirred at room temperature for 30 minutes. The resulting conjugate was purified through size exclusion chromatography on a Bio-Gel P 60 (3×30 cm) column (eluent pH 7 Na₂HPO₄/NaH₂PO₄). The fractions were monitored by iodine assay to identify polymer, and the absorbance at 480 nm was measured to identify doxorubicine. Fractions containing polymer-drug conjugate were collected, ultrafiltered in an Amicon system with a YM 10 membrane to eliminate salts, and the product was freeze dried.

From the absorbance at 480 nm it is evident that PAcM-drug in the final product is 50.6%, with the remainder being inert PAcM-COOH. Experiments demonstrated that the conjugate maintained antitumor activity in the appropriate tumor cell lines.

B. Amoxicillin

Following the method described in part A, PAcM-amoxicillin was obtained. The amount of PAcM-drug conjugate in the final, isolated product (determined through UV spectroscopy) was 70%, with the impurity being PAcM-COOH.

EXAMPLE 14

Preparation of PAcM-lipase and use for bioconversion in organic solvents

The enzyme Candida lipase was modified according to Example 9 to give a lipase-PAcM conjugate in which 65% of the available amino groups were modified. This conjugate was found to be soluble in several organic solvents such as methylene chloride and ethylene chloride. The activity of this conjugate, in these solvents, toward transesterification between vinylbutanol ester and hexanol was shown to be superior to that of the same enzyme which had been modified by PEG as reported in the literature.

EXAMPLE 15

Preparation of PAcM-lipid conjugates: PAcM-distearoylphosphatidyl-ethanolamine PAcM-OH, activated as the p-nitrophenylcarbonate, was dissolved in chloroform and added to a chloroform solution of disteroylphosphatidyl -ethanolamine in a molar ratio of 1 to 3, and the pH was adjusted to 8 by addition of triethylamine (this pH measurement was conducted by placing a drop of the chloroform solution onto a piece of wet pH paper). The solution was maintained at 55° C. for 48 hours. The solution was concentrated by rotary evaporation, and the mixture was purified by precipitation in diethyl ether. Further purification was achieved by recrystallization from absolute ethanol. Product analysis by reverse phase chromatography indicated that the compound was pure (field was about 60%).

EXAMPLE 16

Grafting of PAcM onto inorganic solids: porous glass particles and silica gel A sample of porous glass particles (or silica gel) was dried for 24 hours at 60° C. The particles (10 g) were suspended in toluene (20 ml) and degassed by sonication. γ-Aminopropyl triethoxysilane (10.8 ml) was added, and the suspension was refluxed for 4 hours. The aminated particles were filtered and washed with toluene, ethanol and water before final drying at 40° C. The amine content was evaluated by chloride titration (by the Mohr method), after washing the glass with 1M HCl.

The sample of aminated porous glass particles, or aminated silica gel, (3 g), was suspended in pH 8 borate buffer (0.2M). PAcM-OH (activated as the p-nitrophenylcarbonate —3 g) was added drop by drop with stirring. After 24 hours of gentle stirring the PAcM-grafted particles were filtered and washed with water. The particles were dried and the polymer content was evaluated by ignition, showing 15% by weight polymer. The same grafting procedure was followed with PAcM-COOSu (example 8). In this case, the reaction mixture was stirred for 4 hours, producing similar results.

EXAMPLE 17

Preparation of PAcM-modified nucleosides —a starting material for polynucleotide synthesis 0.5 g of PAcM-COOH (60 μmoles) was dissolved in 2.5 ml of anhydrous methylene chloride. During stirring, 65 μmoles of the nucleoside dimethoxytrityl-deoxythymidine were added. After cooling in an ice bath, 65 μmoles of dicyclohexylcarbodiimide and 65 μmoles of dimethylaminopyridine were added. The reaction was stirred overnight at room temperature. The solution was filtered, and the PAcM-nucleoside precipitated by addition to diethylether. The product was purified by recrystallization from a mixture of methylene chloride and diethylether. Purity was measured by TLC. UV analysis of absorbance of the dimethoxytrityl group revealed 58 μmoles of nucleoside per gram of polymer Yield was 52%.

The invention claimed herein has been described with respect to particular exemplified embodiments. However, the foregoing description is not intended to limit the invention to the exemplified embodiments, and the skilled artisan should recognize that variations can be made within the scope and spirit of the invention as described in the foregoing specification. The invention includes all alternatives, modifications, and equivalents that may be included within the true spirit and scope of the invention as defined by the appended claims.

What is claimed is:

1. Polymeric N-acryloylmorpholine homopolymer having the structure:

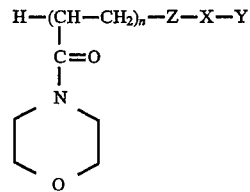

wherein -Z-X-Y is a polymer capping moiety, and in the polymer capping moiety, Y is a reactive moiety, X represents a saturated residue of a linear or branched aliphatic series of the general structure —C$_r$H$_{2r}$— in which r is an integer from 1 to about 12, Z is a moiety that readily reacts to cap a polymer free radical, and n is an integer from about 6 to 280, which yields a number average molecular weight ("M$_n$") of from about 1,000 to 40,000.

2. The polymeric N-acryloylmorpholine according to claim 1 wherein Z; is sulphur, S.

3. The polymeric N-acryloylmorpholine according to claim 1 wherein Y is a reactive moiety selected from the group consisting of —OH, —COOH, and —NH$_2$.

4. The polymeric N-acryloylmorpholine according to claim 1 wherein X is selected from the group consisting of —CH$_2$— and —CH$_2$CH$_2$—.

5. The polymeric N-acryloylmorpholine according to claim 1 wherein the reactive group Y is an active group functional for attachment to a molecule selected from the group consisting of proteins, enzymes, polypeptides, drugs, phospholipids, and nucleosides.

6. A method for synthesizing the polymeric N-acryloylmorpholine homopolymer of claim 1 comprising initiating polymerization of N-acryloylmorpholine monomer and capping the polymer at a number average molecular weight of from about 1,000 to 40,000.

7. The method of claim 6 wherein the step of initiating polymerization comprises adding a free radical initiator to the monomer.

8. The method of claim 7 wherein the initiator is azobisisobutyronitrile.

9. The method of claim 6 wherein the step of capping the polymer comprises adding a chain terminating agent to the monomer in a concentration sufficient to control the molecular weight of the polymer.

10. The method of claim 9 wherein the chain terminating agent is mercaptan and has the structure Y-X-SH, wherein Y is a reactive moiety and X represents a saturated residue of a linear or branched aliphatic series of the general structure —C$_r$H$_{2r}$— in which r is an integer from 1 to about 12.

11. The method of claim 10 further comprising the step of reacting the polymer with a compound to form a reactive moiety that is active for selective attachment to surfaces and molecules.

12. Polymeric N-acryloylmorpholine homopolymer having the structure:

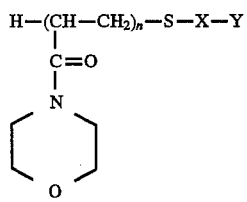

wherein -S-X-Y is a polymer capping moiety, and in the polymer capping moiety, Y is a reactive moiety, X represents a saturated residue of a linear or branched aliphatic series of the general structure —$C_rH_{2r}$— in which r is an integer from 1 to about 12, and n is an integer from about 6 to 280, which yields a number average molecular weight: ("$M_n$") of from about 1,000 to 40,000.

13. The polymeric N-acryloylmorpholine according to claim 12 wherein Y is a reactive moiety selected from the group consisting of —OH, —COOH, and —$NH_2$.

14. The polymeric N-acryloylmorpholine according to claim 13 wherein Y is a reactive moiety selected from the group consisting of succinimide, p-nitrophenyl, and trichlorophenyl.

15. The polymeric N-acryloylmorpholine according to claim 12 wherein Y is a reactive moiety selected from the group consisting of chemically active ester moieties suitable for direct coupling to amine moieties, chemically active carbonate moieties suitable for direct coupling to amine moieties, aldehydes, imminoesters, and epoxide.

16. The polymeric N-acryloylmorpholine according to claim 12 wherein Y is a reactive moiety selected from the group consisting of chemically active moieties suitable for direct coupling to thiol moieties.

17. The polymeric N-acryloylmorpholine according to claim 16 wherein Y is selected from the group consisting of vinylsulfone, maleimide, iodoacetamide, vinylpyridine, dithiopyridine, and thiol.

18. Polymeric N-acryloylmorpholine homopolyer having the structure:

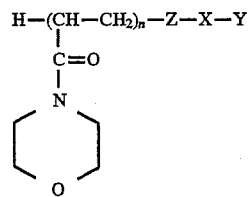

wherein -Z-X-Y is a polymer capping moiety, and in the polymer capping moiety, Y is a reactive moiety selected from the group consisting of succinimide, p-nitrophenyl, and trichlorophenyl; X represents a saturated residue of a linear or branched aliphatic series of the general structure —$C_rH_{2r}$— in which r is an integer from 1 to about 12; Z is a moiety that readily reacts to cap a polymer free radical; and n is an integer from about 6 to 280, which yields a number average molecular weight ("$M_n$") of from about 1,000 to 40,000.

19. Polymeric N-acryloylmorpholine homopolyer having the structure:

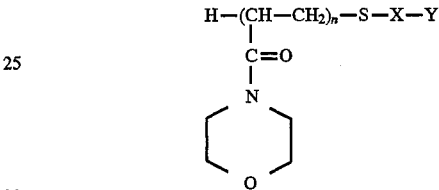

wherein -S-X-Y is a polymer capping moiety, and in the polymer capping moiety, Y is a reactive moiety selected from the group consisting of succinimide, p-nitrophenyl, and trichlorophenyl; X represents a saturated residue of a linear or branched aliphatic series of the general structure —$C_rH_{2r}$— in which r is an integer from 1 to about 12; and n is an integer from about 6 to 280, which yields a number average molecular weight ("$M_n$") of from about 1,000 to 40,000.

* * * * *

UNITED STATES PATENT AND TRADEMARK OFFICE
CERTIFICATE OF CORRECTION

PATENT NO. : 5,629,384                           Page 1 of 4
DATED : May 13, 1997
INVENTOR(S) : Veronese et al.

It is certified that error appears in the above-identified patent and that said Letters Patent is hereby corrected as shown below:

On the title page, column 1, inventor's address, line 2, "Padua" should be -- Padova --.

Column 1, line 29, "increase" should be -- have increased --.

Column 1, line 29, "decrease" should be -- decreased --.

Column 1, line 48, "Film" should be -- Films --.

Column 1, line 57, "System" should be -- Systems --.

Column 2, line 14, after "4" insert -- , --.

Column 2, line 15, after "(1986)" insert -- , --.

Column 2, line 30, "Amphilic" should be -- Amphiphilic --.

Column 2, line 31, "protein" should be -- proteins --.

Column 3, line 15, before "group" insert a space.

Column 3, line 33, after "N'" insert a dash (-).

Column 3, line 48, after "as" insert -- a --.

UNITED STATES PATENT AND TRADEMARK OFFICE
CERTIFICATE OF CORRECTION

PATENT NO. : 5,629,384
DATED : May 13, 1997
INVENTOR(S) : Veronese et al.

It is certified that error appears in the above-identified patent and that said Letters Patent is hereby corrected as shown below:

Column 4, line 36, "NH2)" should be -- $NH_2$) --.

Column 4, line 55, "0,005M)" should be -- 0.005M) --.

Column 5, line 1, "0,025" should be -- 0.025 --.

Column 5, line 23 (Example 3), "$CH_{2-NH2}$" should be -- $CH_2$-$NH_2$ --.

Column 5, line 48, "P 60" should be -- P60 --.

Column 6, line 18, "$CL_2$" should be -- $Cl_2$ --.

Column 6, line 44, "Sec 30" should be -- Sec30 --.

Column 8, line 23, "Of" should be -- of --.

Column 8, line 36, begin new line with "catalase:".

Column 8, line 65, "polymerenzyme" should be -- polymer-enzyme --.

Column 9, line 1, "DMP" should be -- DPM --.

Column 9, line 1, before "was" insert -- (decompositions per minute) --.

Column 9, line 2, after "0.5" omit the comma (,).

Column 9, line 16, "DMP" should be -- DPM --.

UNITED STATES PATENT AND TRADEMARK OFFICE
CERTIFICATE OF CORRECTION

PATENT NO. : 5,629,384

DATED : May 13, 1997

INVENTOR(S) : Veronese et al.

It is certified that error appears in the above-identified patent and that said Letters Patent is hereby corrected as shown below:

Column 9, lines 30-33, omit "Pharmacokinetic profiles for native enzymes and enzyme-polymer conjugates are given in FIGS. 1 and 2.

Column 9, line 64, "10.15M" should be -- 0.15M --.

Column 10, line 4, after "washed" insert -- 3 --.

Column 10, line 6, after "evaluated" omit the period (.).

Column 10, lines 8-9, omit "are given in FIGS. 4 and 5. These Figures".

Column 11, line 16, "field" should be -- yield --.

Column 12, line 5, "homopolyer" should be -- homopolymer --.

Column 12, line 27, after "Z" omit the semicolon (;).

Column 12, line 41, "homopolyer" should be -- homopolymer --.

Column 12, line 66, "homopolyer" should be -- homopolymer --.

Column 13, line 31, "imminoesters" should be -- iminoesters --.

Column 13, line 41, "homopolyer" should be -- homopolymer --.

UNITED STATES PATENT AND TRADEMARK OFFICE
CERTIFICATE OF CORRECTION

PATENT NO. : 5,629,384
DATED : May 13, 1997
INVENTOR(S) : Veronese et al.

It is certified that error appears in the above-identified patent and that said Letters Patent is hereby corrected as shown below:

Column 14, line 20, "homopolyer" should be -- homopolymer --.

Signed and Sealed this

Twenty-first Day of October 1997

Attest:

BRUCE LEHMAN

Attesting Officer

Commissioner of Patents and Trademarks